(12) United States Patent
Ansari et al.

(10) Patent No.: US 8,666,541 B1
(45) Date of Patent: Mar. 4, 2014

(54) SYSTEM AND METHOD FOR CHECKING THE ACCURACY OF A PRESCRIPTION FILL

(75) Inventors: Mohsin Ovais Ansari, Highland Park, IL (US); Michael J. Simko, Palos Heights, IL (US); Laura Jean Tebbe, Antioch, IL (US); Russell Alan Wielgos, Wauconda, IL (US)

(73) Assignee: Walgreen Co., Deerfield, IL (US)

( * ) Notice: Subject to any disclaimer, the term of this patent is extended or adjusted under 35 U.S.C. 154(b) by 72 days.

(21) Appl. No.: 13/528,435

(22) Filed: Jun. 20, 2012

Related U.S. Application Data

(62) Division of application No. 12/877,593, filed on Sep. 8, 2010, now Pat. No. 8,224,483, which is a division of application No. 10/920,606, filed on Aug. 18, 2004, now Pat. No. 7,801,642.

(51) Int. Cl.
*G06F 17/00* (2006.01)

(52) U.S. Cl.
USPC ........... 700/240; 700/237; 700/232; 700/215; 700/216; 700/305

(58) Field of Classification Search
USPC ........... 700/216, 231–244, 305; 235/375, 385
See application file for complete search history.

(56) References Cited

U.S. PATENT DOCUMENTS

| | | |
|---|---|---|
| 5,337,919 A | 8/1994 | Spaulding et al. |
| 5,597,995 A | 1/1997 | Williams et al. |
| 5,619,991 A | 4/1997 | Sloane |
| 5,737,539 A | 4/1998 | Edelson et al. |
| 5,758,095 A | 5/1998 | Albaum et al. |
| 5,790,785 A | 8/1998 | Klug et al. |
| 5,797,515 A | 8/1998 | Liff et al. |
| 5,801,755 A | 9/1998 | Echerer |
| 5,845,255 A | 12/1998 | Mayaud |
| 5,852,259 A | 12/1998 | Yanase |

(Continued)

FOREIGN PATENT DOCUMENTS

| | | |
|---|---|---|
| EP | 0 921 488 A1 | 6/1999 |
| WO | WO-96/13790 A1 | 5/1996 |
| WO | WO-01/08393 A1 | 2/2001 |

OTHER PUBLICATIONS

Colchamiro, "Independents Look to Go Online," American Druggist, Sep. 1999, pp. 1-3.

(Continued)

*Primary Examiner* — Michael K Collins
(74) *Attorney, Agent, or Firm* — Francis C. Kowalik; Marshall, Gerstein & Borun LLP; Randall G. Rueth

(57) ABSTRACT

A method of checking the accuracy of a prescription fill including activating an electronic scale operatively coupled to a network, accessing a prescription to fill; selecting an appropriate stock container corresponding to the prescription from a plurality of available stock containers, entering data that is associated with a stock container selected by the user; determining if the stock container selected by the user is the correct stock container to fill the prescription by determining if the drug corresponding to the selected stock container is the appropriate drug for the accessed prescription; retrieving a piece weight of the drug from the selected stock container; measuring a weight of a plurality of pills to be dispensed; comparing the measured weight of the pills to be dispensed to a standard weight; determining if the comparison is within an acceptable range; and generating an automated authorization for the prescription fill.

19 Claims, 14 Drawing Sheets

(56) References Cited

U.S. PATENT DOCUMENTS

| | | | |
|---|---|---|---|
| 5,883,370 | A | 3/1999 | Walker et al. |
| 5,907,493 | A | 5/1999 | Boyer et al. |
| 5,911,687 | A | 6/1999 | Sato et al. |
| 5,915,240 | A | 6/1999 | Karpf |
| 5,924,074 | A | 7/1999 | Evans |
| 5,946,883 | A | 9/1999 | Yuyama et al. |
| 5,954,640 | A | 9/1999 | Szabo |
| 5,970,462 | A | 10/1999 | Reichert |
| 5,987,519 | A | 11/1999 | Peifer et al. |
| 6,067,524 | A | 5/2000 | Byerly et al. |
| 6,202,923 | B1 | 3/2001 | Boyer et al. |
| 6,208,973 | B1 | 3/2001 | Boyer et al. |
| 6,294,999 | B1 | 9/2001 | Yarin et al. |
| 6,311,163 | B1 | 10/2001 | Sheehan et al. |
| 6,330,491 | B1 | 12/2001 | Lion |
| 6,347,329 | B1 | 2/2002 | Evans |
| 6,364,517 | B1 | 4/2002 | Yuyama et al. |
| 6,370,841 | B1 | 4/2002 | Chudy et al. |
| 6,381,577 | B1 | 4/2002 | Brown |
| 6,397,190 | B1 | 5/2002 | Goetz |
| 6,421,650 | B1 | 7/2002 | Goetz et al. |
| 6,438,451 | B1 | 8/2002 | Lion |
| 6,463,417 | B1 | 10/2002 | Schoenberg |
| 6,464,142 | B1 | 10/2002 | Denenberg et al. |
| 6,477,442 | B1 | 11/2002 | Valerino, Sr. |
| 6,493,427 | B1 | 12/2002 | Kobylevsky et al. |
| 6,523,009 | B1 | 2/2003 | Wilkins |
| 6,539,281 | B2 | 3/2003 | Wan et al. |
| 6,564,121 | B1 | 5/2003 | Wallace et al. |
| 6,625,925 | B1 | 9/2003 | Foster |
| 6,650,964 | B2 | 11/2003 | Spano, Jr. et al. |
| 6,671,579 | B2 | 12/2003 | Spano, Jr. et al. |
| 6,707,381 | B1 | 3/2004 | Maloney |
| 6,711,460 | B1 | 3/2004 | Reese |
| 6,874,684 | B1 | 4/2005 | Denenberg et al. |
| 7,111,780 | B2 | 9/2006 | Broussard et al. |
| 7,139,639 | B2 | 11/2006 | Broussard et al. |
| 7,801,642 | B2 * | 9/2010 | Ansari et al. ............. 700/240 |
| 8,224,483 | B1 * | 7/2012 | Ansari et al. ............. 700/240 |
| 2002/0062175 | A1 | 5/2002 | Lion |
| 2002/0062230 | A1 | 5/2002 | Morag et al. |
| 2002/0120573 | A1 | 8/2002 | McCormick |
| 2002/0153411 | A1 | 10/2002 | Wan et al. |
| 2002/0188467 | A1 | 12/2002 | Eke |
| 2003/0074234 | A1 | 4/2003 | Stasny |
| 2003/0149599 | A1 | 8/2003 | Goodall et al. |
| 2003/0179287 | A1 | 9/2003 | Kozic et al. |
| 2004/0133705 | A1 | 7/2004 | Broussard et al. |
| 2004/0220829 | A1 | 11/2004 | Baharav et al. |
| 2004/0221034 | A1 | 11/2004 | Kausik et al. |
| 2004/0260577 | A1 | 12/2004 | Dahlin et al. |
| 2005/0113969 | A1 | 5/2005 | Spano et al. |
| 2006/0041330 | A1 | 2/2006 | Ansari et al. |
| 2006/0276933 | A1 | 12/2006 | Chavez et al. |

OTHER PUBLICATIONS

McNaughton, "Can Net Drugstores Outpace The Chains?" CNET News.com, Feb. 24, 1999, 1 page.

Wolverton, "Online Pharmacies Partner for Power," CNET News. com, Oct. 8, 1999, pp. 1-2.

"The Virtual Pharmacist," *Rural Electric*, vol. 60, No. 6, Mar. 2002, p. 20.

U.S. Appl. No. 11/253,252, filed Oct. 18, 2005, entitled "System for Separating and Distributing Pharmacy Order Processing."

U.S. Appl. No. 11/252,759, filed Oct. 18, 2005, entitled "System for Separating and Distributing Pharmacy Order Processing for Medication Payments."

U.S. Appl. No. 09/715,872, filed Nov. 15, 2000, entitled "Apparatus and Method for Accessing Pharmacy Information and Ordering Prescriptions."

U.S. Appl. No. 11/252,776, filed Oct. 18, 2005, entitled "System for Separating and Distributing Pharmacy Order Processing for Specialty Medication."

U.S. Appl. No. 11/253,185, filed Oct. 18, 2005, entitled "System for Separating and Distributing Pharmacy Order Processing for Prescription Verification."

U.S. Appl. No. 11/253,253, filed Oct. 18, 2005, entitled "System for Separating and Distributing Pharmacy Order Processing for Out of Stock Medication."

U.S. Appl. No. 11/252,947, filed Oct. 18, 2005, entitled "System for Separating and Distributing Pharmacy Order Processing for Compound Medication."

U.S. Appl. No. 11/252,775, filed Oct. 18, 2005, entitled "Method and Apparatus for Inter-Pharmacy Workload Balancing."

Office Action for U.S. Appl. No. 10/920,606 dated Apr. 6, 2007.
Office Action for U.S. Appl. No. 10/920,606 dated May 2, 2007.
Office Action for U.S. Appl. No. 10/920,606 dated Nov. 27, 2007.
Office Action for U.S. Appl. No. 10/920,606 dated Aug. 1, 2008.
Office Action for U.S. Appl. No. 10/920,606 dated Jul. 23, 2009.

* cited by examiner

SYSTEM AND METHOD FOR CHECKING THE ACCURACY OF A PRESCRIPTION FILL

CROSS-REFERENCE TO RELATED APPLICATIONS

This application is a divisional of U.S. application Ser. No. 10/920,606, filed Aug. 18, 2004 and U.S. application Ser. No. 12/877,593 filed Sep. 8, 2010, the disclosures of which are hereby incorporated herein by reference in their entirety for all purposes.

TECHNICAL FIELD

The present patent relates generally to techniques for checking the accuracy of a prescription fill in a pharmacy, and more particularly to checking that a correct drug is selected and ensuring that the correct amount of the drug is placed into a container by checking the weight of the drug.

BACKGROUND

In traditional pharmacies, pharmacists and technicians are responsible for repetitively filling large numbers of prescriptions. Because of the necessary human intervention in traditional prescription fill processes, a small percentage of prescriptions are filled inaccurately. The inaccuracies may result in a wrong drug being placed in a medication vial and given to a patient or a wrong quantity of a drug being placed in a medication vial, or both. Either of these occurrences could result in a serious impact on the health of a patient. As a result, a system is needed to reduce the number of filling errors by creating a system that enables a systematic process to be implemented within a pharmacy to verify the drug and check the quantity, in a majority of the prescriptions filled.

DETAILED DESCRIPTION OF VARIOUS EMBODIMENTS

Figure 1:
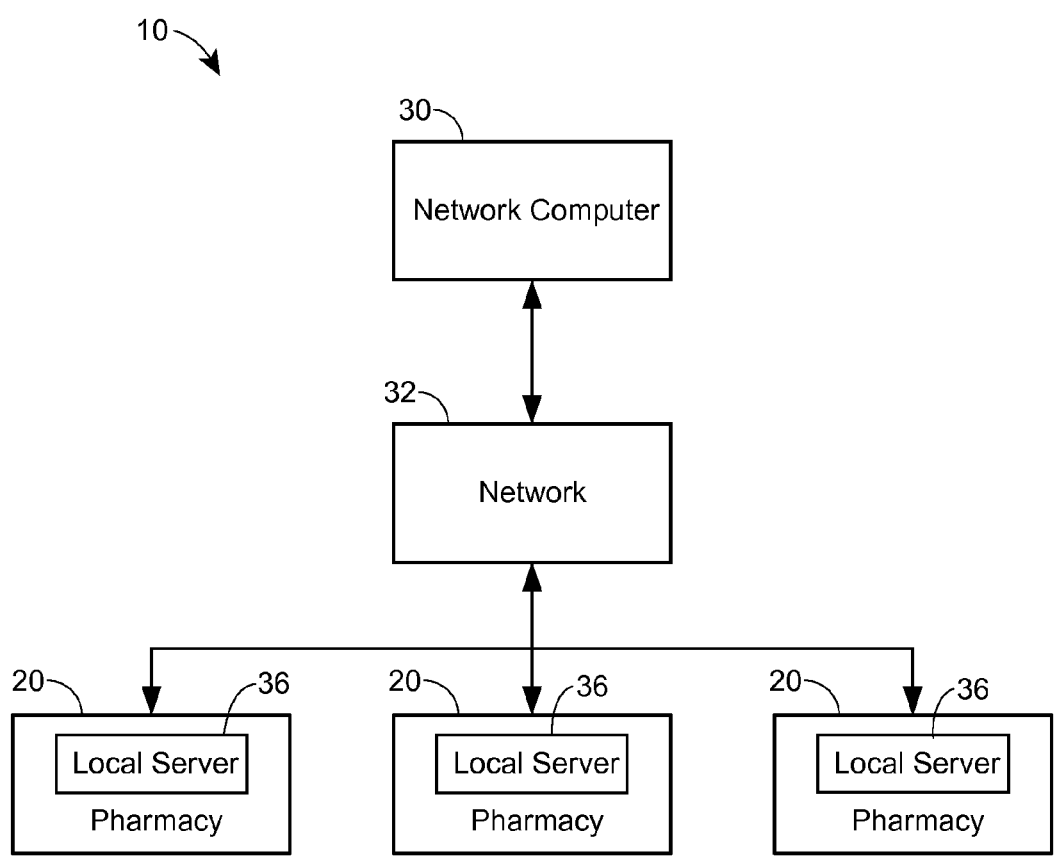
FIG. 1 is a block diagram of an embodiment of an intelligent network system.

FIG. 1 illustrates an embodiment of a data network 10 that may be used to ensure the accuracy of a large number of prescription fills that occur throughout several pharmacies that are each located in different geographic locations. Referring to FIG. 1, the data network 10 may include a first group of pharmacies or facilities 20 operatively coupled to a network computer or machine 30 via a network 32. The plurality of pharmacies 20 may be located, by way of example rather than limitation, in separate geographic locations from each other, in different areas of the same city, or in different states. Also, the pharmacies 20 may be affiliated with a single entity or with multiple entities. The pharmacies 20 may be located in a conventional retail store or they may be located in proximity with a drug warehouse or distribution center that would a shipping facility and would not be accessible to the general public. The network computer or machine 30 may also include or may be connected to a central drug/product database, discussed in greater detail below with reference to FIG. 2.

The network 32 may be provided using a wide variety of techniques well known to those skilled in the art for the transfer of electronic data. For example, the network 32 may comprise dedicated access lines, plain, ordinary telephone lines, satellite links, combinations of these, etc. Additionally, the network 32 may include a plurality of network computers or server computers (not shown), each of which may be operatively interconnected in a known manner. Where the network 32 comprises the Internet, data communication may take place over the network 32 via an Internet communication protocol.

The network computer 30 may be a server computer of the type commonly employed in networking solutions, and it may also have a data structure into which customer account data and prescription fill data is retained. The network computer 30 may be used to accumulate, analyze, and download data relating to the operation of the pharmacies 20 and more particularly to information pertaining to drugs, weights of those drugs, other data corresponding to those drugs, and the accuracy of prescriptions filled at the pharmacies 20. For example, the network computer 30 may periodically receive data from each of the pharmacies 20 indicative of prescriptions filled that were verified or authorized and prescriptions filled that were, for various reasons, not verified. This information may be accumulated and periodically transferred to an off-site facility for purposes of data storage, report generation, etc. The pharmacies 20 may include one or more local servers 36 that may be utilized to store information on drugs, the weights of those drugs, and other information pertaining to those drugs. For example, the local servers 36 may store information pertaining to the supply or availability of the drugs at the local pharmacy 36, or to identifiers used with the drugs, such as, for example, barcodes, Radio Frequency ID (RFID) tags, or National Drug Codes (NDCs). The local servers 36 may also store information related to prescriptions filled at the pharmacy 36 that may be used to generate a wide variety of reports, such as, for example, error reports, override reports, etc.

Additionally, the local servers 36 may store and run an application that determines if a stock container containing a drug that corresponds to a particular prescription and is selected by a pharmacy employee is the correct stock container to fill the prescription. The application may also compare a measures weight of a drug in a prescription to a standard or predicted total weight of the drug in a prescription to ensure that the correct amount of the drug is dispersed for the prescription. These determinations and comparisons are described in greater detail below with reference to the flowcharts.

Although the data network 10 is shown to include one network computer 30 and three pharmacies 20, it should be understood that different numbers of computers and pharmacies may be utilized. For example, the network 32 may include a plurality of network computers 30 and hundreds or thousands of pharmacies 20, all of which may be interconnected via the network 32. According to the disclosed example, this configuration may provide several advantages, such as, for example, enabling near real time uploads and downloads of information as well as periodic uploads and downloads of information. This provides for a primary backup of all the information generated in transactions where prescriptions are verified and filled.

Figure 2:
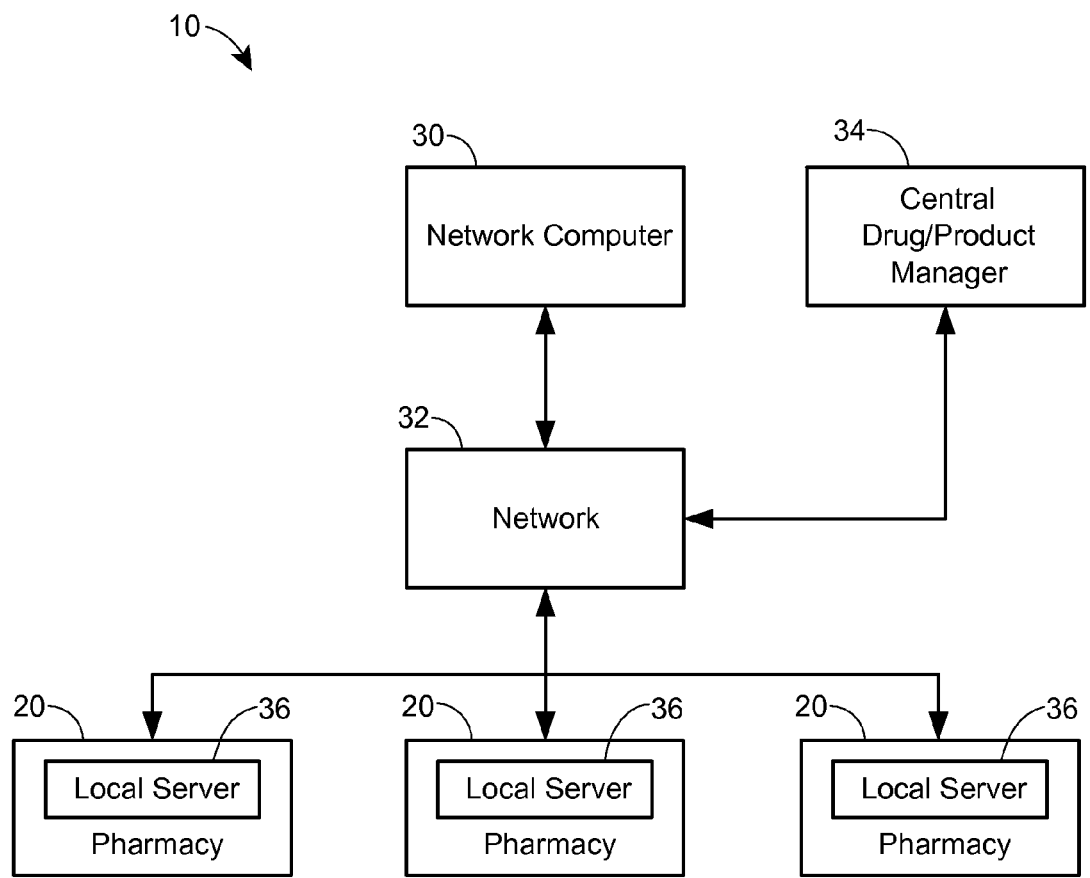
FIG. 2 is a block diagram of an alternative embodiment of an intelligent network system that includes a central drug/product database.

FIG. 2 illustrates an alternative embodiment of the network 10 shown in FIG. 1, wherein a central drug/product manager 34 is used to manage the drugs and weights of those drugs, and possibly the identifiers used for those drugs, such as barcodes, RFID tag data, or NDCs. The central drug/product manager 34 is shown separately in FIG. 2, but could be a functional entity implemented on the network computer 30 as shown in FIG. 1, or elsewhere. The embodiment of FIG. 2 is similar to the embodiment shown in FIG. 1 and includes many of the same structures and components. For clarity, the structures and components remaining the same are shown with like reference numbers as those from FIG. 1. Referring to FIG. 2, the drug/product manager 34 may be linked to the network 32 so that data may be transferred between the drug/product manager 34 and the network computer 30 and the pharmacies 20.

The drug/product manager 34 may be used as a repository to store information pertaining to drugs, weights of those drugs, other data corresponding to those drugs, and the accuracy of prescriptions filled at the pharmacies 20. As with the network computer 30 in FIG. 1, the drug/product manager 34 may periodically receive data from each of the pharmacies 20 indicative of prescriptions filled that were verified or authorized and prescriptions filled that were either verified or not. The drug/product manager 34 may be an unrelated third party, or it may be a subsidiary or division of the owner of the pharmacies.

Figure 3:
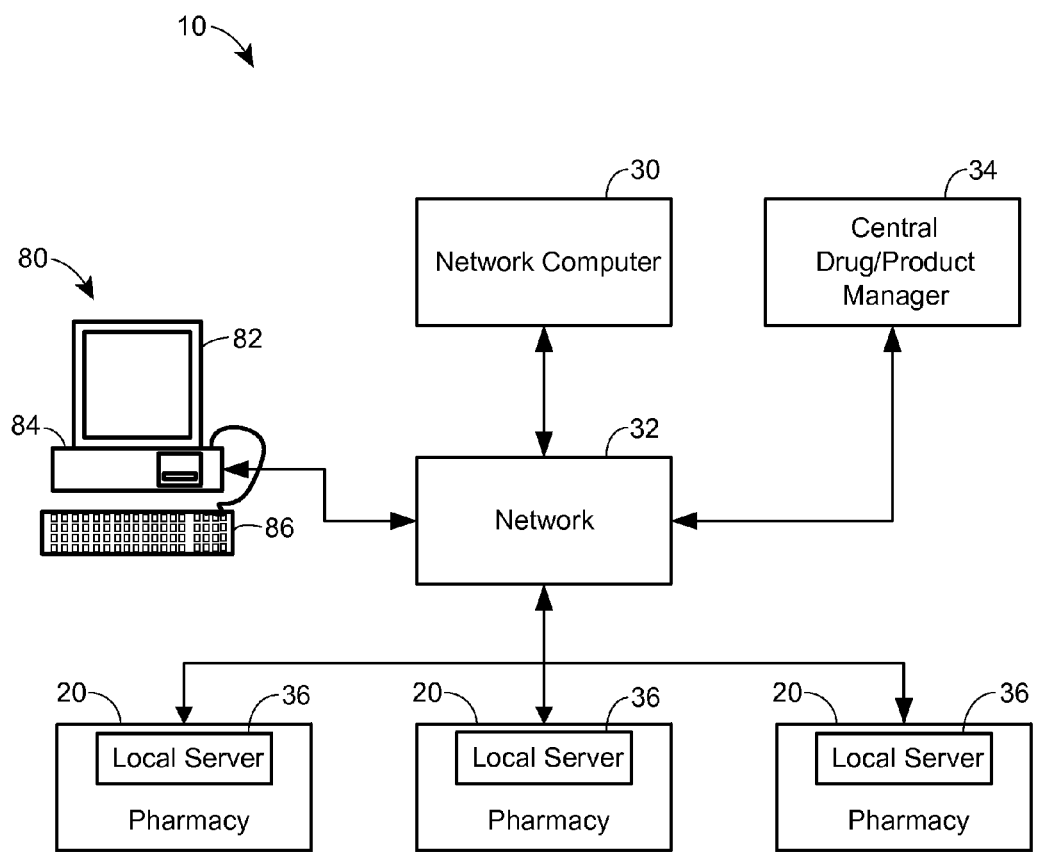
FIG. 3 is a block diagram of an alternative embodiment of an intelligent network system that includes a connected client device.

FIG. 3 illustrates an alternative embodiment of the network 10 shown in FIG. 1, wherein a client device 80 is linked to the network 32 to enable a customer to order a prescription to be filled using the client device 80. The embodiment of FIG. 3 is similar to the embodiment shown in FIGS. 1 and 2 and includes many of the same structures and components. For clarity, the structures and components remaining the same are shown with like reference numbers as those from FIGS. 1 and 2.

Referring to FIG. 3, the client device 80 may be any suitable device for accessing the network 32, such as a computer, PDA, web enabled cell phone, etc., and is shown to include a display 82, a controller 84, a keyboard 86, as well as a variety of other input/output devices. The client device 80 may be linked to the network 32 so that a customer may order a prescription to be filled without having to physically visit one of the pharmacies 20. The pharmacy organization may provide the customer the option of having the prescription drug(s) shipped to the customer or having the prescription drug(s) made available at a local (or any other) retail pharmacy 20 for pickup by the customer.

While the network 10 is shown to include one network computer 30, one drug/product manager 34, three pharmacies 20, and one client device 80, it should be understood that different numbers of computers, pharmacies, and client devices may be utilized. For example, the network 32 may include a plurality of network computers 30, a plurality of drug/product managers 34 and or databases, hundreds or thousands of pharmacies 20, and a plurality of client devices 80, all of which may be interconnected via the network 32.

Figure 4:
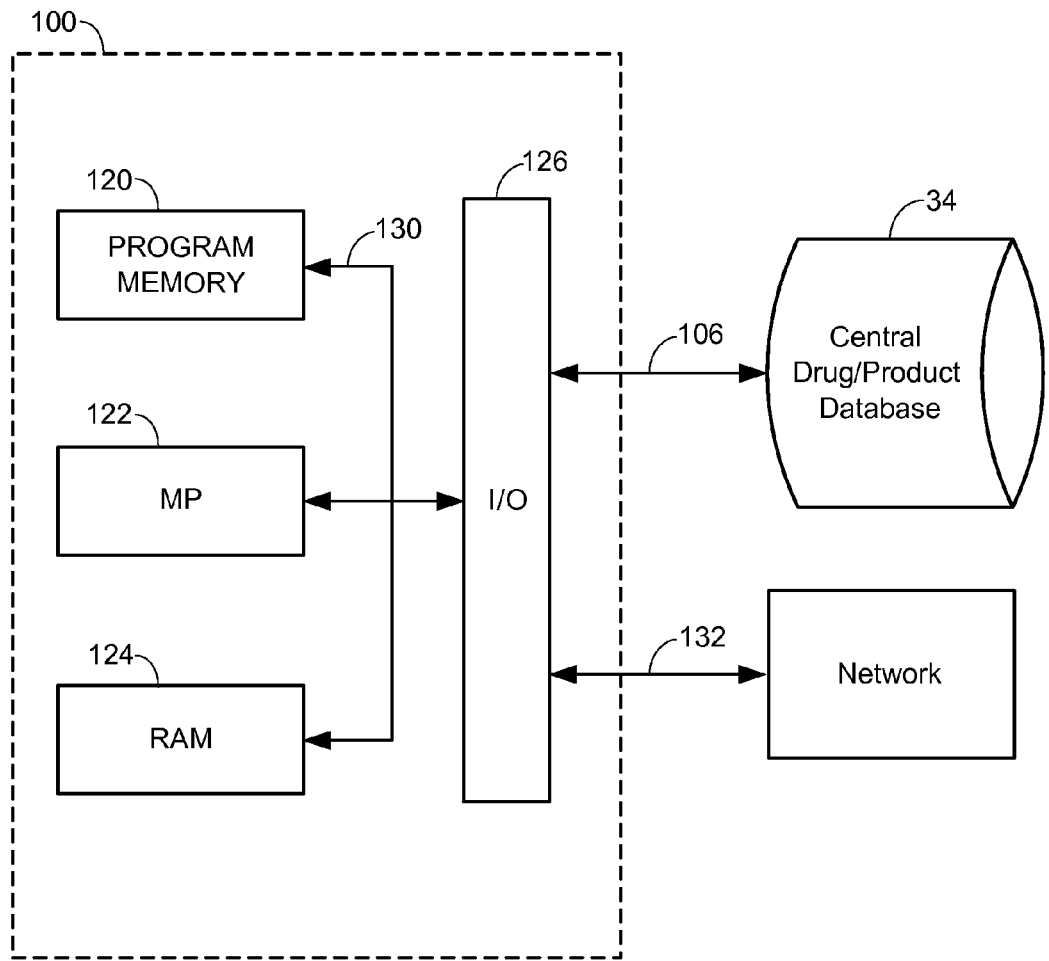
FIG. 4 is a schematic diagram of some of the components of the network computer shown in FIGS. 1, 2, and 3.

FIG. 4 is a schematic diagram of one possible embodiment of the network computer 30 shown in FIGS. 1, 2, and 3. The network computer 30 may have a controller 100 that is operatively connected to a drug/product database 102 via a link 106. It should be noted that, while not shown, additional databases may be linked to the controller 100 in a known manner.

The controller 100 may include a program memory 120, a microcontroller or a microprocessor (MP) 122, a random-access memory (RAM) 124, and an input/output (I/O) circuit 126, all of which may be interconnected via an address/data bus 130. It should be appreciated that although only one microprocessor 122 is shown, the controller 100 may include multiple microprocessors 122. Similarly, the memory of the controller 100 may include multiple RAMs 124 and multiple program memories 120. Although the I/O circuit 126 is shown as a single block, it should be appreciated that the I/O circuit 126 may include a number of different types of I/O circuits. The RAM(s) 124 and programs memories 120 may be implemented as semiconductor memories, magnetically readable memories, and/or optically readable memories, for example. All of these memories or data repositories may be referred to as machine-accessible mediums. The controller 100 may also be operatively connected to the network 32 via a link 130.

For the purpose of this description and as briefly discussed above, a machine-accessible medium includes any mechanism that provides (i.e., stores and/or transmits) information in a form accessible by a machine (e.g., a computer, network device, personal digital assistant, manufacturing tool, any device with a set of one or more processors). For example, a machine-accessible medium includes recordable/non-recordable media (e.g., read only memory (ROM); random access memory (RAM); magnetic disk storage media; optical storage media; flash memory devices), as well as electrical, optical, acoustical or other form of propagated signals (e.g., carrier waves, infrared signals, digital signals); etc.

Figure 5:
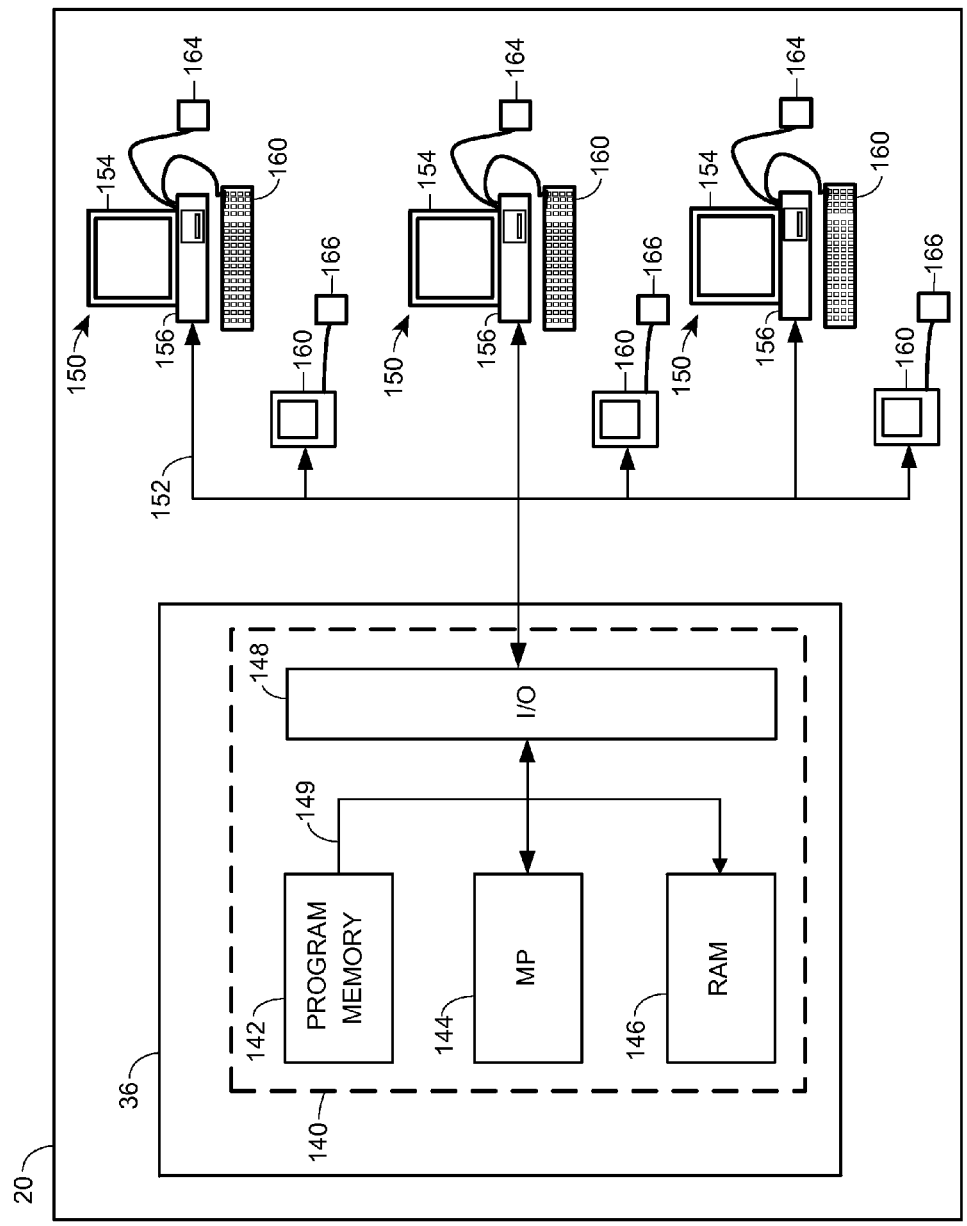
FIG. 5 is a schematic diagram of an embodiment of one of the facilities shown schematically in FIGS. 1, 2, and 3.

FIG. 5 is a schematic diagram of one possible embodiment of several components located in one or more of the pharmacies 20 from FIGS. 1, 2, and 3. Although the following description addresses the design of the pharmacies 20, it should be understood that the design of one or more of the pharmacies 20 may be different than the design of other pharmacies 20. Also, each pharmacy 20 may have various different structures and methods of operation. It should also be understood that the embodiment shown in FIG. 5 illustrates some of the components and data connections present in a pharmacy 20, however it does not illustrate all of the data connections present in a typical retail store in which the pharmacy is part of (i.e., a photo department, a cosmetic department, a plurality of front line terminals, etc.). For exemplary purposes, various designs of the pharmacies are described below, but it should be understood that numerous other designs may be utilized.

The pharmacy 20 may have a local server 36, which includes a controller 140, wherein the local server 36 is operatively connected to a plurality of computers 150 via a network 152. The network 152 may be a wide area network (WAN), a local area network (LAN), or any other type of network readily known to those persons of ordinary skill in the art. The computers 150 may also be operatively connected to the network computer 30 as illustrated in FIGS. 1-3 via the network 32.

Similar to the controller 100 from FIG. 4, the controller 140 may include a program memory 142, a microcontroller or a microprocessor (MP) 144, a random-access memory (RAM) 146, and an input/output (I/O) circuit 148, all of which may be interconnected via an address/data bus 149. As discussed with reference to the controller 100, it should be appreciated that although only one microprocessor 144 is shown, the controller 140 may include multiple microprocessors 144. Similarly, the memory of the controller 140 may include multiple RAMs 146 and multiple programs memories 142. Although the I/O circuit 148 is shown as a single block, the I/O circuit 148 may include a number of different types of I/O circuits. The RAM(s) 146 and programs memories 142 may also be implemented as semiconductor memories, magnetically readable memories, and/or optically readable memories, for example.

The computers 150 may include a display 154, a controller 156, a keyboard 160, an RFID tag reader 164, as well as a variety of other input/output devices such as a mouse, touch screen, track pad, track ball, isopoint, printer, card reader, voice recognition system, a keypad, a biometrics device (such as an iris reader or fingerprint scanner), etc. Coupled to either the network 152 or the computers 150 is an electronic scale 166 and a barcode scanner 170 (either stationary or portable and either wired or wireless). With regard to the RFID tag reader 164 and the barcode scanner 170, as discussed below, each of these devices may be eliminated in some of the disclosed embodiments. Each computer 150 may be signed onto and occupied by a pharmacy employee to assist them in performing their duties. Pharmacy employees may sign onto a computer 150 using any generically available technique, such as entering a user name and password, using an ID card, or inputting biometric data. If a pharmacy employee is required to sign onto a computer 150, this information may be passed via the link 152 to the local server 36 so that the controller 140 will be able to identify the signed on pharmacy employees and the corresponding computer 150. This may be useful in monitoring the pharmacy employees' prescription fill performance. Pharmacy employees may also sign onto an electronic scale 166 using a similarly generic technique, such as entering a user name and password, using an ID card, or inputting biometric data. If the pharmacy employee is required to sign onto a scale 160, this information may also be passed via the link 152 to the local server 36 so that the controller 140 will be able to identify the signed on pharmacy employees and the corresponding scale 160.

Typically, local servers 36 store a plurality of files, programs, and other data for use by the computers 150, the scales 160, and the network computer 30. One local server 36 may handle requests for drug information and weights for those drugs from a large number of POS terminals 150. Accordingly, each local server 36 may typically comprise a high end computer with a large storage capacity, one or more fast microprocessors, and one or more high speed network connections. Conversely, relative to a typical local server 36, each computer 150 may typically include less storage capacity, a single microprocessor, and a single network connection.

Overall Operation of the System

One manner in which an exemplary system may operate is described below in connection with a number of flow charts which represent a number of portions or routines of one or more computer programs. As those of ordinary skill in the art will appreciate, the majority of the software utilized to implement the routines is stored in one or more of the memories in the controllers 100 and 140, and may be written at any high level language such as C, C++, C#, Java or the like, or any low-level assembly or machine language. By storing the computer program portions therein, various portions of the memories are physically and/or structurally configured in accordance with the computer program instructions. Parts of the software, however, may be stored and run locally on the terminals 150. As the precise location where the steps are executed can be varied without departing from the scope of the invention, the following figures do not address the machine performing an identified function.

Figure 6A:
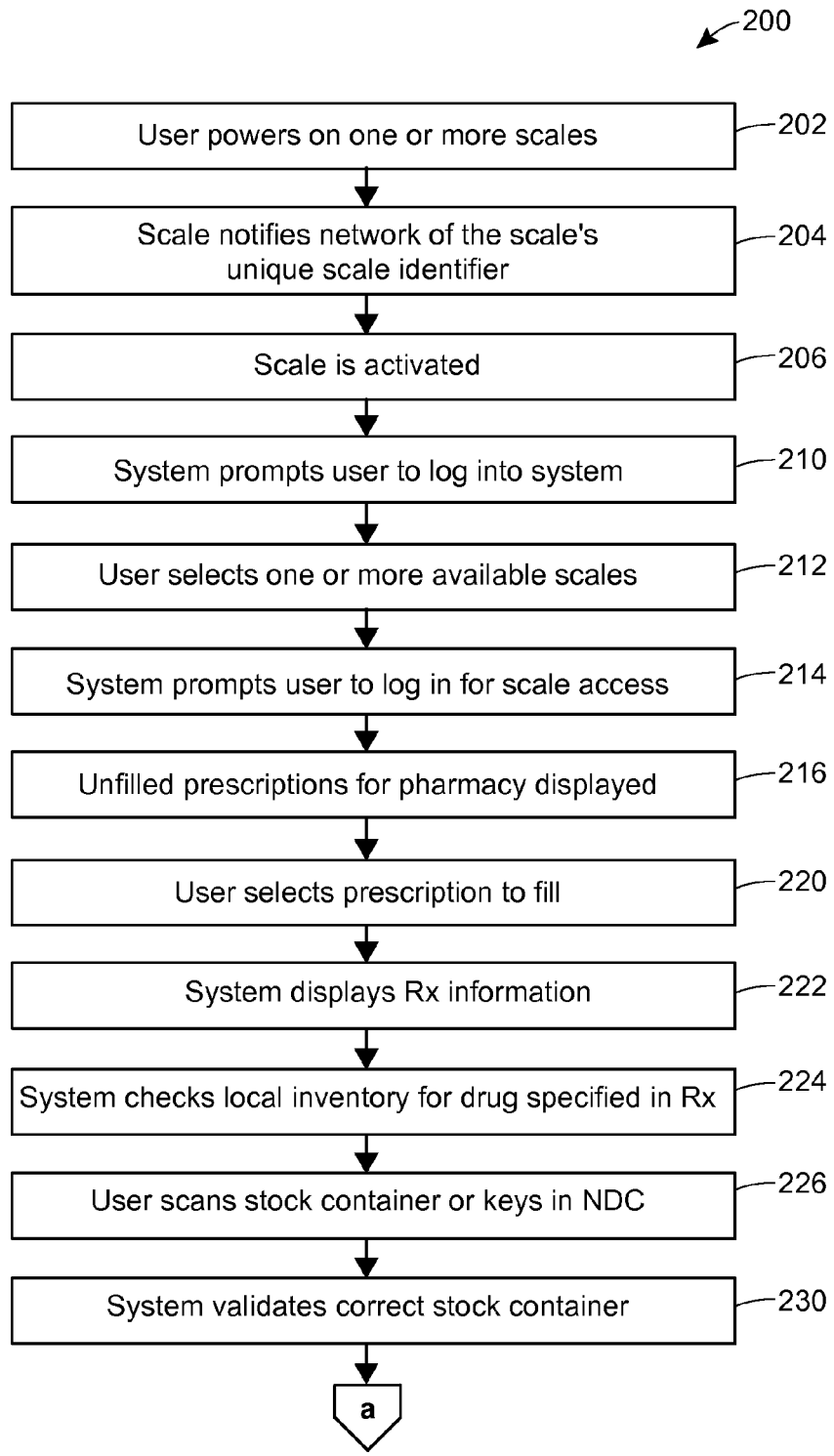
FIGS. 6A and 6B are two parts of a flowchart showing some of the steps used to facilitate checking the accuracy of a prescription fill.
Figure 6B:
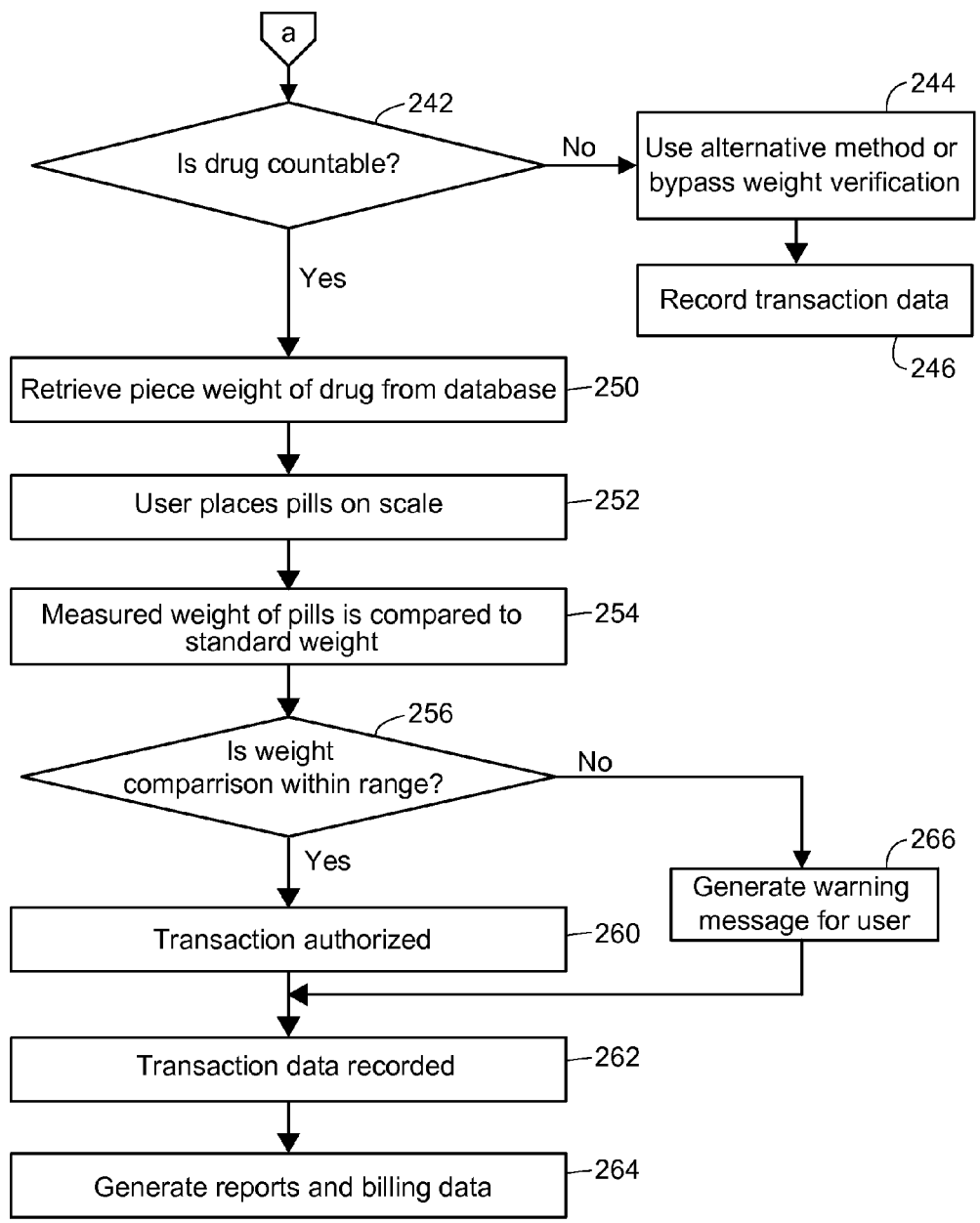

FIGS. 6A and 6B are two parts of a flow chart 200 describing some of the steps used to reduce the number of errors in filling a prescription by verifying the drug selected by a pharmacy employee to fill the prescription and by verifying the quantity of the drug portioned by the pharmacy employee from a stock container for the drug. Some of the steps shown in the flowchart 200 may be stored in the memory of the controllers 100 and 140.

Referring to FIG. 6A, the flowchart 200 may begin when a pharmacy employee powers on one of the electronic scales 166 (block 202). The electronic sale 166 may be configured so that the scale's unique scale identifier is transmitted via the network 152 to the local server 36 (block 204). The scale 166 may also transmit its unique scale identifier to the network computer 30 via the network 32. The unique scale identifier may be, for example, an alphanumeric code comprising a number of digitals where a portion of those digits may be used to identify a geographical location of the scale 166. The unique scale address may be included as part of the scale's ip address, such as 10.1.10.xxx.

Once the scale identifier for the scale 166 has been transmitted to the local server 36, the system may then activate the electronic scale 166 (block 206). The system may then update a database to indicate that the electronic scale 166 is available.

When a pharmacy employee wishes to fill a prescription, the system may prompt the pharmacy employee to log into the system (block 210) which may include a request for a user ID and password or some type of biometric data. Once proper login information has been submitted to the system, a desktop may appear that includes a number of buttons to select available electronic scales 166. The pharmacy employee may then select one or more of the available scales by selecting the scale(s) on the employee's desktop (block 212). After selecting a scale to access, the system may prompt the pharmacy employee to login again for access to a particular electronic scale 166 (block 214). The system may then check to ensure that the scale 166 selected by the pharmacy employee is available.

Once the pharmacy employee has been granted access one or more of the electronic scales 166, the system may display on a terminal display 154 a list of unfilled prescriptions for the local pharmacy 20 (block 216).

Using a mouse, touch screen, or other input device, the pharmacy employee may select a prescription to fill from the list of unfilled prescriptions displayed on the terminal 154

(block 220). The system may then display various information corresponding to the prescription selected by the pharmacy employee that would include, for example, the drug or the stock container for the drug that is to be used in filling the prescription (block 222). The system may then check a local inventory for an availability of the drug specified in the prescription (block 224).

The system may then provide the pharmacy employee with the ability to cause data to be entered that is associated with the stock container selected by the user, wherein the stock container contains the drug corresponding to the prescription that is to be filled (block 226). Depending on the type of drug identifier placed on the stock container, this step of entering data associated with a stock container may include, for example, scanning a barcode on the stock container with the use of the barcode scanner 170, positioning an RFID tag on the stock container in proximity of the RFID tag reader 164, or entering an NDC code for the drug in the stock container with the use of either the keyboard 160 or a separate keypad. Once the pharmacy employee scans the barcode on the label on the stock container, or keys in an NDC, or positions an RFID tag, the system may determine if the stock container selected by the pharmacy employee is the correct stock container to fill the prescription (block 230).

As shown in FIG. 6B the system may then determine if the drug is countable (block 242). If it is determined at the block 242 is not countable, the pharmacy employee may use an alternative method or simply bypass a weight verification and proceed with filling the prescription after receiving only the stock container validation (244). The system may then record data associated with the transaction for the purposes of generating subsequent reports (block 242).

If it is determined at the block 242 that the drug is countable, the system may retrieve a piece weight of the drug corresponding to the prescription from a local database in the local server 36 (block 250). The piece weight of the drug may alternatively be located in the network computer 30 or the central drug/product manager 34. If the drug is in the form of pills, the pharmacy employee may place what the pharmacy employee believes is appropriate number of pills on the electronic scale 166 and measure the weight of those pills (block 252).

The system may then compare the weight of the pills to a standard weight, wherein the standard weight equals a predicted total weight of the plurality of pills. This predicted weight may is sometimes referred to as the theoretical value. The system may then determine if the comparison is within an acceptable or predetermined range (block 256). For example, the system may determine if the weight measured by the electronic scale 166 is within a certain percentage of the predicted total weight of the pills. Alternatively, the system may determine if the weight measured by the electronic scale 166 is within a predetermined threshold, either plus or minus, of the predicted total weight.

If the weight comparison was within an acceptable range, the system may generate an authorization for this prescription fill (block 260). The system may then record data associated with the transaction (block 262) and use that data to generate a variety of reports and billing data (block 264). If it was determined at the block 256 that the weight comparison was not within an acceptable range, the system may generate a warning message for the user (block 266) and allow the pharmacy employee to either correct the error, or proceed with filling the transaction without an authorization.

If the system is not able to retrieve data corresponding to either the drug, the stock container or the weight of the drug, the pharmacy employee may be permitted to override the system and fill the prescription without a system generated authorization. The system may be further configured to allow the pharmacy employee to provide a reason for the override so that subsequent override reports may be generated that provide meaningful information to the pharmacy enterprise. A plethora of additional reports could also be generated which could include, a detailed report itemizing all authorizations and all override transactions for a particular pharmacy employee, as well as a variety of metrics measuring performance based on scale usage statistics. Lastly, while not shown in FIG. 6, when a pharmacy employee logs off a scale 166, the system may update the scale database to indicate that the scale 166 is available for a subsequent sign-on.

It should be noted that the logic to provide the functionality described in most of the blocks shown in FIGS. 6A and 6B will most likely reside on the local server 36. However, those of ordinary skill in the art will understand that the logic associated with those steps, as well as any of the other steps described in flowchart 200 may reside in any of the other computers/controllers connected to the network 32.

Those of ordinary skill in the art will readily appreciate that if the embodiment shown in FIG. 2 or 3 are used, the drug data and any transaction data may be transmitted between the local server 36 and the drug/product manager 34. For the sake of simplicity, the remainder of this description will focus primarily on systems shown in FIG. 1 that do not include a drug/product manager.

Figure 7A:
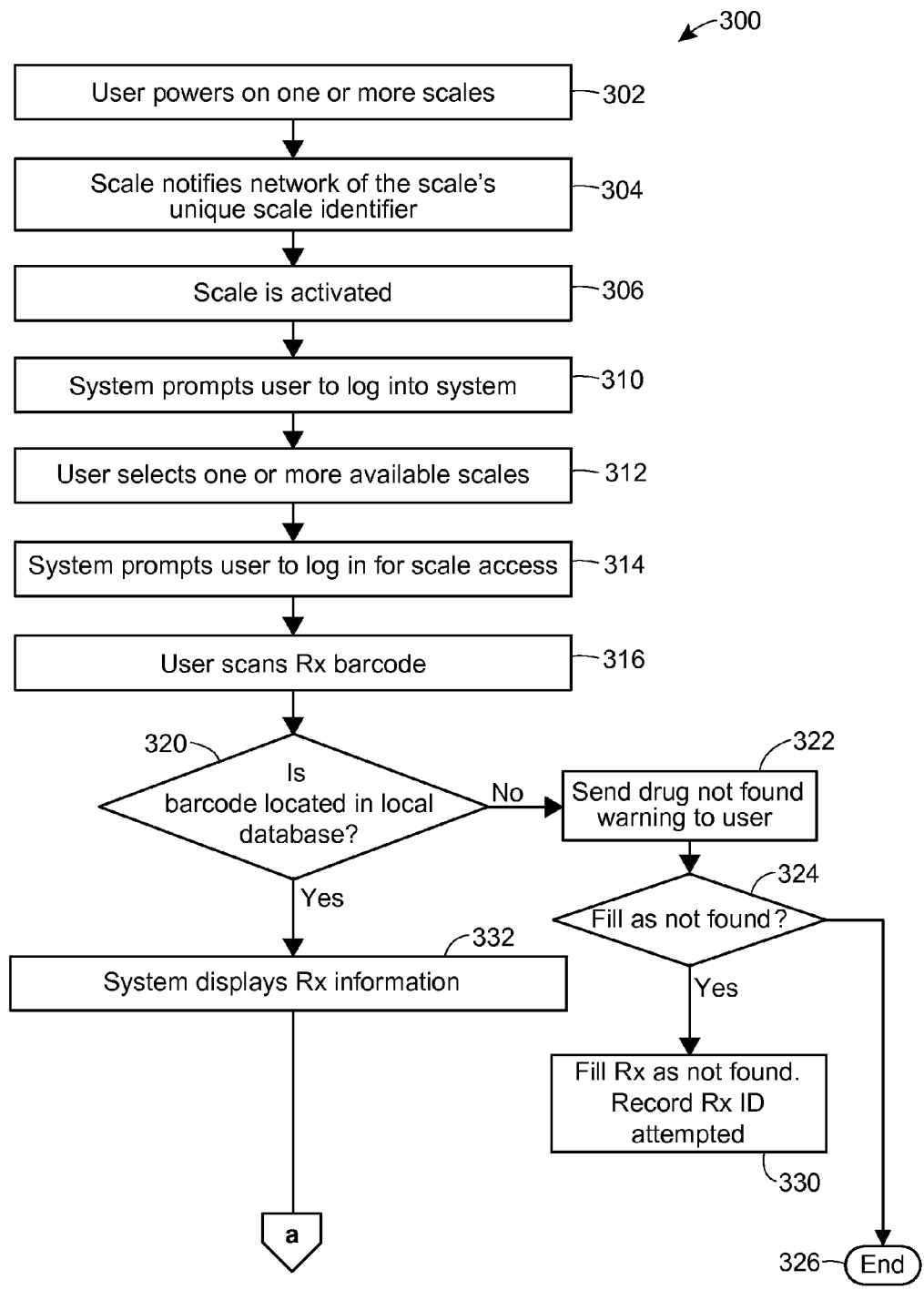
FIGS. 7A and 7B are two parts of a flowchart showing some of the steps used in an alternative embodiment to the embodiment shown in FIGS. 6A and 6B and includes barcode technology.
Figure 7B:
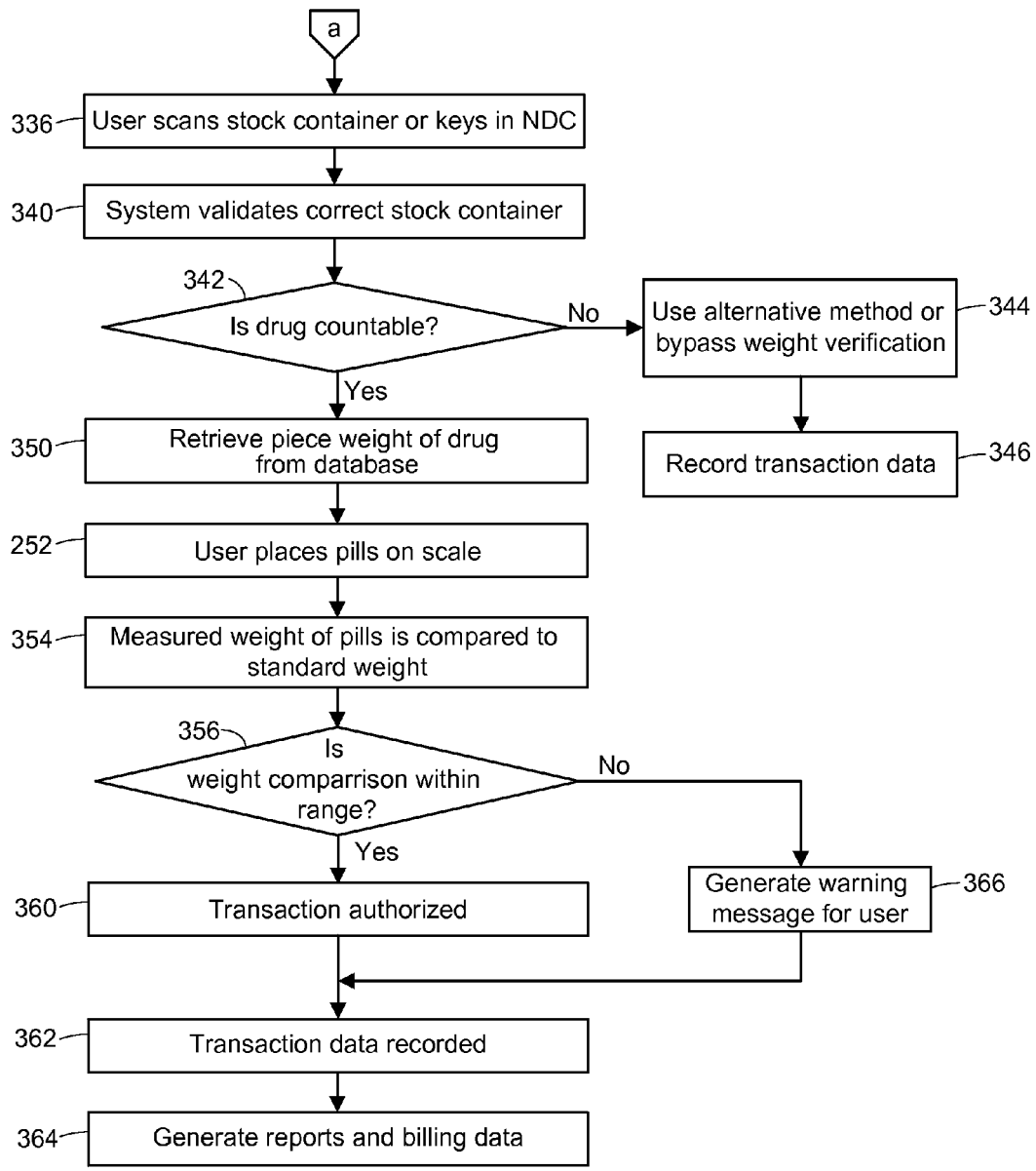

FIGS. 7A and 7B are two parts of a flow chart 300 describing some of the steps used to facilitate using barcode technology to check the accuracy of a prescription fill. The flowchart 300 is similar to the flowchart 200 from FIGS. 6A and 6B except that it includes scanning a prescription barcode from a prescription label to obtain information about a prescription for a pharmacy to fill.

Referring to FIG. 7A, the system may begin when a user powers on one or more of the scales 166 (block 302). The system may be configured so that the scale 166 notifies the network 152 and the local server 36 of the scale's unique identifier (block 304). Once aware of the newly powered on scale 166, the system may activate the scale 166 for use by a pharmacy employee (block 306). Before allowing a pharmacy employee to access one of the scales 166, the system may require the pharmacy employee to provide login information in the form of a user ID and password by prompting the user to log in to the system (block 310). Biometric information corresponding to the pharmacy employee may also be provided.

If the system determines that the user has the appropriate authorization to access one of the scales 166, the user may be permitted to select one or more of the available scales 166 with the use of a mouse or other input device (block 312). The system may then prompt the pharmacy employee for a second set of login information for access to the scale 166 selected by the pharmacy employee (block 314). The system may then indicate to all other users on the system that the scale 166 selected by the pharmacy employee is no longer available for access by another pharmacy employee.

After determining that the pharmacy employee has authorization to access the scale 166, the system provides the pharmacy employee with the ability to cause data to be entered that is associated with a prescription, by allowing the pharmacy employee to scan a prescription barcode using the barcode scanner 170 (block 316). The system may then look to a database in the local server 36 for a set of data associated with the prescription barcode (block 320). The system could also be adapted to look to the network computer 30 or the central drug product manager 34 for information corresponding to the prescription barcode if the prescription barcode is not located in the local server 36.

If the system is not able to locate information corresponding to the prescription barcode, the system may send a 'drug not found' warning to the user (block 322). The system may then inquire with the pharmacy employee as to whether or not he or she wishes to proceed with filling the prescription (block 324). If the pharmacy employee does not what to continue, the transaction may be terminated (block 326).

If it is determined at the block 324 that the pharmacy employee wishes to proceed with filling the prescription, the system may generate an entry indicating that the prescription was attempted and filled as not found (block 330).

If it is determined at the block 320 that the prescription barcode was located, the system may retrieve a set of data associated with the prescription barcode and display the set of data to the pharmacy employee on one of the displays 154 (block 332). The system may also check and inventory at the pharmacy for availability of the drug in the prescription.

As shown in FIG. 7B, the system may then permit the pharmacy employee to select a stock container containing a drug corresponding to the prescription and scan a barcode located on the stock container with the barcode scanner 170 (block 336). If there is no barcode on the stock container of if the barcode on the stock container is not readable, the system may allow the pharmacy employee to key in the NDC corresponding to the drug in the stock container through a keypad. The system may then determine if the stock container selected by the pharmacy employee is a correct stock container to fill the prescription (block 340).

The system may then proceed to determine if the drug in the prescription is countable (block 342). If it is determined at the block 342 that the drug is not countable, the pharmacy employee may be given an alternative method to check the weight of the drug or bypass the weight verification process (block 344). The system may then record transaction data associated with the alternative method or the bypass/override (block 346).

If it is determined at the block 342 that the drug is countable, the system may retrieve a piece weight of the drug from a database stored on the local server 36, the network computer 20, the central drug product manager 34, or any other suitable location (block 350). The pharmacy employee may then remove from the stock container a number of pills corresponding to the prescription and place those pills on the electronic scale 166 (block 352). The system may then measure the weight of the pills on the electronic scale 166 and compare the measured weight of the pills to the weight equaling a predicted total weight of the plurality of pills (block 354). As previously stated in reference to FIG. 6B, the predicted total weight of the plurality of the pills is the weight obtained from the database and is sometimes referred to as a standard weight or a theoretical value.

The system may then determine if the weight comparison is within an acceptable range (block 356) and generate a warning message for the user if the weight comparison is outside of the acceptable range (366). If it is determined at the block 356 that the weight comparison is within an acceptable range, the system may validate the transaction by generating an authorization for the prescription fill (block 360). Thereafter, the system may record data associated with the transaction (block 362) that allows for the future generation of reports and billing data (block 364). As previously stated a plethora of reports may be generated from the transaction data associated with each prescription filled such as, for example, generating an override report for prescriptions filled at the pharmacy that did not have authorizations generated. Metrics measuring performance based on scale usage statistics may also be incorporated.

It should be noted that the pharmacy 20 may give a customer the option to access an account record for the customer by permitting electronic access to the pharmacy's website through the terminal 80. Access to the pharmacy's website may be available via the Internet, where a customer may enter his/her customer ID to access his/her account record for a variety of reasons. For example, a patient may wish to place an order for a prescription over the Internet without having to physically visit the pharmacy, or the customer may wish to check to see if a prescription order has been authorized, filled, and made available for pickup or shipping by the pharmacy. The pharmacy may also provide the customer access to the system to allow prescriptions to be ordered or to allow the status of a prescription to be checked via a toll-free telephone number.

Figure 8A:
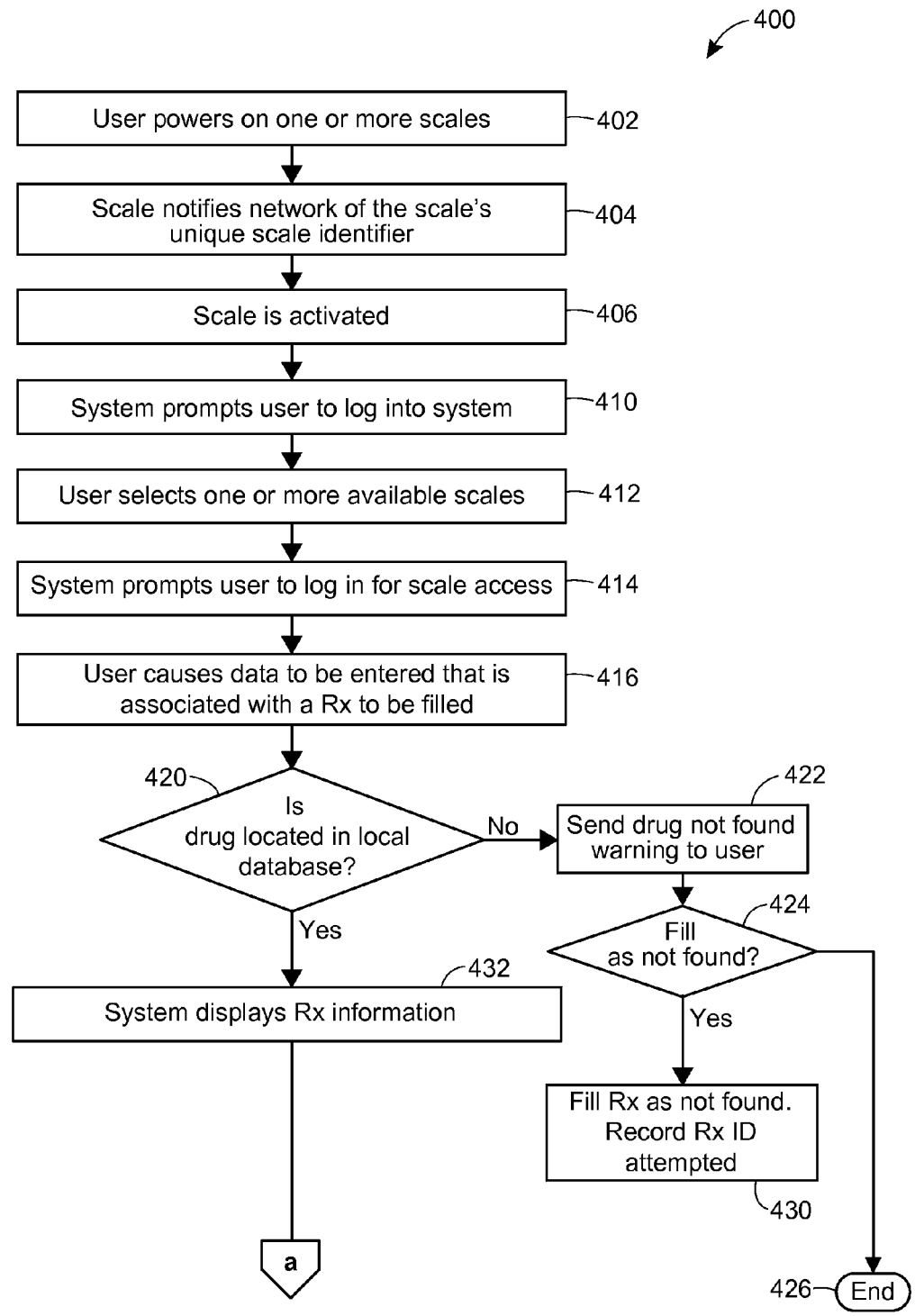
FIGS. 8A and 8B are two parts of a flowchart showing some of the steps used in another alternative embodiment to the embodiment shown in FIGS. 6A and 6B and includes RFID technology.
Figure 8B:
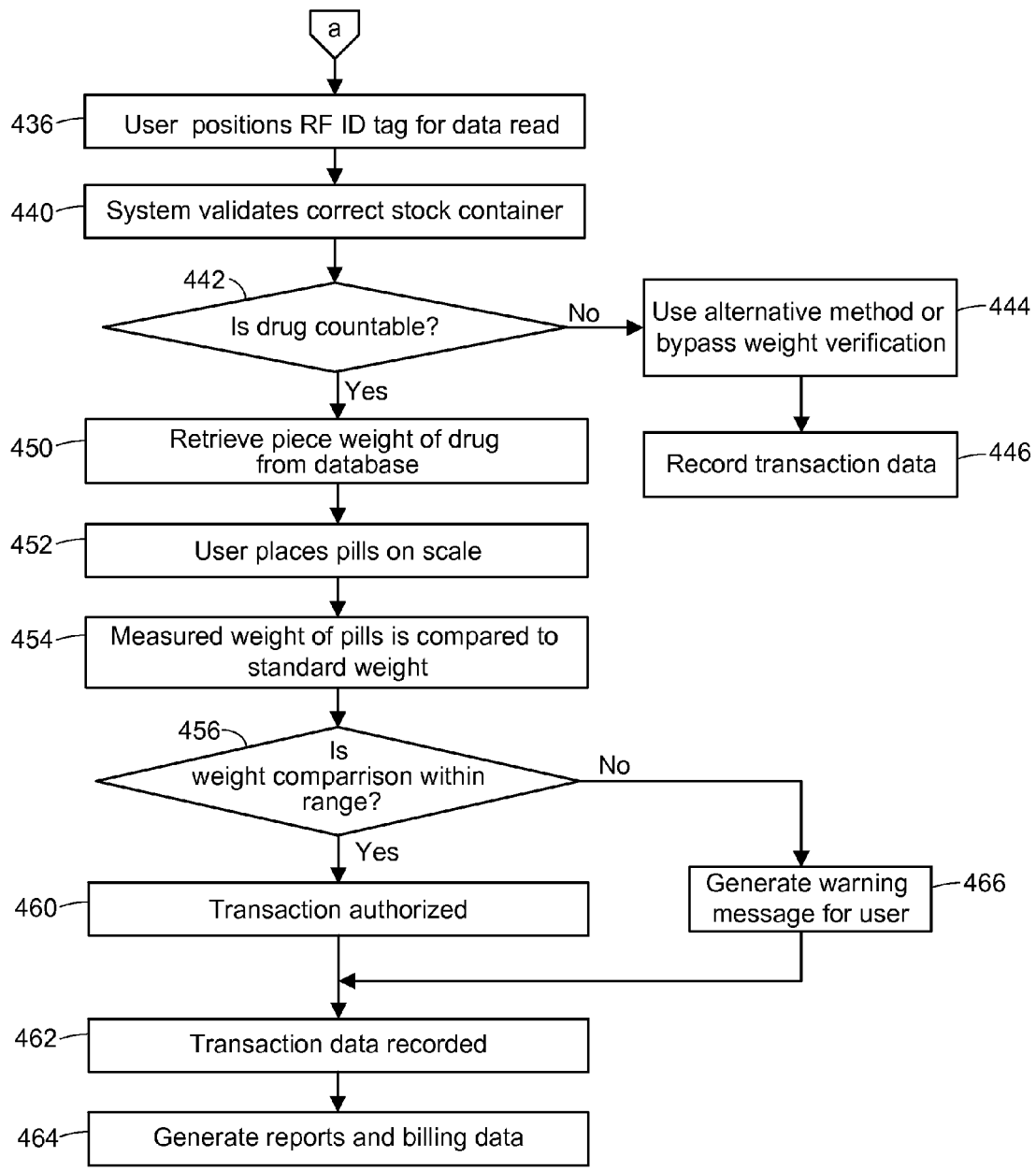

FIGS. 8A and 8B are two parts of a flowchart 400 describing some of the steps used to reduce a number of errors in filling a prescription by verifying the drug selected by a pharmacy employee to fill the prescription and by verifying the quantity of the drug portioned by the pharmacy employee from a stock container corresponding to the drug. Some of the steps shown in the flowchart 400 may be stored in the memory of the controllers 100 and 140.

Referring to FIG. 8A, the flowchart 400 may begin when a pharmacy employee powers on one of the electronic scales 166 (block 402). The scale 166 may be adapted to notify the local server 36 via the network 152 when the scale is powered on (block 404). An application running on the local server 36 may then activate the electronic scale 166 for access by pharmacy employees (block 406). In order to access the system, a pharmacy employee may be required to provide login or biometric information (block 410).

After accessing the system, the pharmacy employee may select one or more of the available scales (block 412). Before allowing access to the scale, the system may also prompt the pharmacy employee to log in for scale access or to provide biometric data (block 414). The system may then provide the user with the ability to cause data to be entered that is associated with a prescription (block 416). The pharmacy employee may cause data to be entered by, for example, selecting a prescription listed on the display 150, scanning a barcode associated with the prescription, positioning an RFID tag corresponding to the prescription so that the RFID tag is read by the RFID tag read 164, entering an NDC associating with the prescription, or any other technique known to those of ordinary skill in the art.

The system will then determine if the drug associated with the prescription to be filled is located in a local database (block 420). If the drug is not located in a local database, the system may generate and send a 'drug not found' warning to the pharmacy employee (block 422). The system may then prompt the pharmacy employee to determine if the prescription should proceed to be filled without an authorization (block 424). If the pharmacy employee does not want to continue, the system may terminate the transaction (block 426). If it is determined at the block 424 that the pharmacy employee wants to fill the prescription, the system will permit the pharmacy employee to proceed and record a prescription ID associated with the attempted prescription fill (block 430).

If it determined at the block 420 that the drug is located in the local database, the system may check an inventory at the pharmacy for an availability of the drug and the prescription and display a set of data associated with the prescription to the pharmacy employee on the display 154 (block 432).

As shown in FIG. 8B the pharmacy employee may locate a stock container for the drug in the prescription and position the stock container so that an RFID tag secured to the stock container may be read by the RFID tag reader 164 (block 436). The application running on the local server 36 may then determine if the stock container selected by the pharmacy employee is the correct stock container to fill the prescription (block 440). The system may then determine if the drug is countable (block 442). If the drug is not countable, the pharmacy employee may use an alternative method to ensure that the proper amount of the drug is portioned when filling the prescription (block 444) and the system will then record data associated with the transaction (block 446).

If it is determined at the block 442 that the drug is countable, the system may retrieve a piece weight of the drug in the prescription from a database (block 450) and the pharmacy employee may place a number of pills on the scale 166 for measurement (block 452). The measured weight of the plurality of pills is then compared to a standard weight, the standard weight equals a predicted total weight of the plurality of pills (block 454).

The system may then determine if the comparison is within an acceptable range (block 456). If it is determined at the block 456 that the weight comparison is within an acceptable range, the system may generate an authorization for the prescription fill (block 460). Transaction data associated with the prescription fill may then be recorded (block 462) and the system may utilize the recorded data in generating a number of reports and billing data (block 464). If it is determined at the block 456 that the weight comparison was not within an acceptable range, the system may generate a warning message for the user (block 466).

Figure 9:
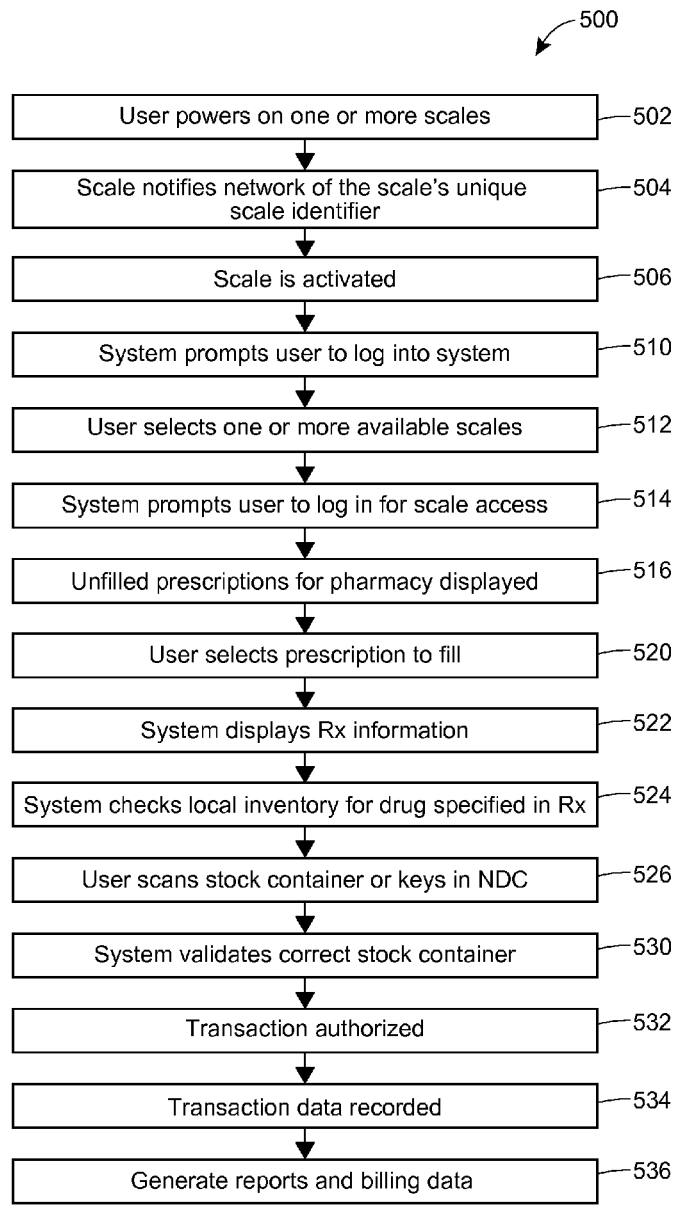
FIG. 9 is a flowchart showing some of the steps used in another alternative embodiment to check if a correct stock container has been used to fill a prescription.

FIG. 9 is a flowchart 500 describing some of the steps to check if a correct stock container has been used to fill a prescription. The flowchart 500 may begin when a pharmacy employee powers one of the electronic scales 166 (block 502). The scale 166 may be adapted to notify the local server 36 via the network 152 upon initialization (block 504). This may include transmitting the scale's unique identifier. The system may then activate the scale 166 for access by a pharmacy employee (block 506). To access the system, a pharmacy employee may be required to provide login information or biometric data to the system (block 510).

After gaining access to the system, the pharmacy employee may select one or more of the available scales 166 to use in filling prescriptions (block 512). After selecting one or more of the scales, the pharmacy employee may be prompted for biometric or login information in order to access the scales (block 514). At this time, the system may display at least a portion of unfilled prescriptions for the pharmacy on the display 154 (block 516). The pharmacy employee may then use an input device such as a mouse to select one of the prescriptions to fill (block 520).

After a pharmacy employee has selected a particular prescription to fill, the system may display a set of data associated with the prescription on the display 154 (block 522). The system may also check a local inventory for the drug specified in the prescription for its availability (block 524).

The system may then provide the pharmacy employee with the ability to cause data to be entered that is associated with a stock container that has been selected by the pharmacy employee, wherein the stock container contains a drug corresponding to the prescription (block 526). This may include scanning a barcode on the stock container, keying in an NDC, positioning an RFID tag to be read by the RFID reader 164, or any other method generally known to those of ordinary skill in the art. The system may then determine if the stock container selected by the pharmacy employee is the correct stock container to fill the prescription (block 530).

If the stock container selected by the pharmacy employee is validated, the system may generate an authorization for the transaction (block 532). Thereafter, the system may record data associated with the transaction (block 534) that may be accessed in generating a number of reports and billing data (block 536). Metrics measuring performance based on scale usage statistics may also be incorporated. It should be noted that the transaction data for the prescriptions authorized and filled may be stored in a memory associated with the local server 36. The information may also be periodically transferred to the network computer 30 and/or the central drug product manager 34 via the network 32.

Figure 10A:
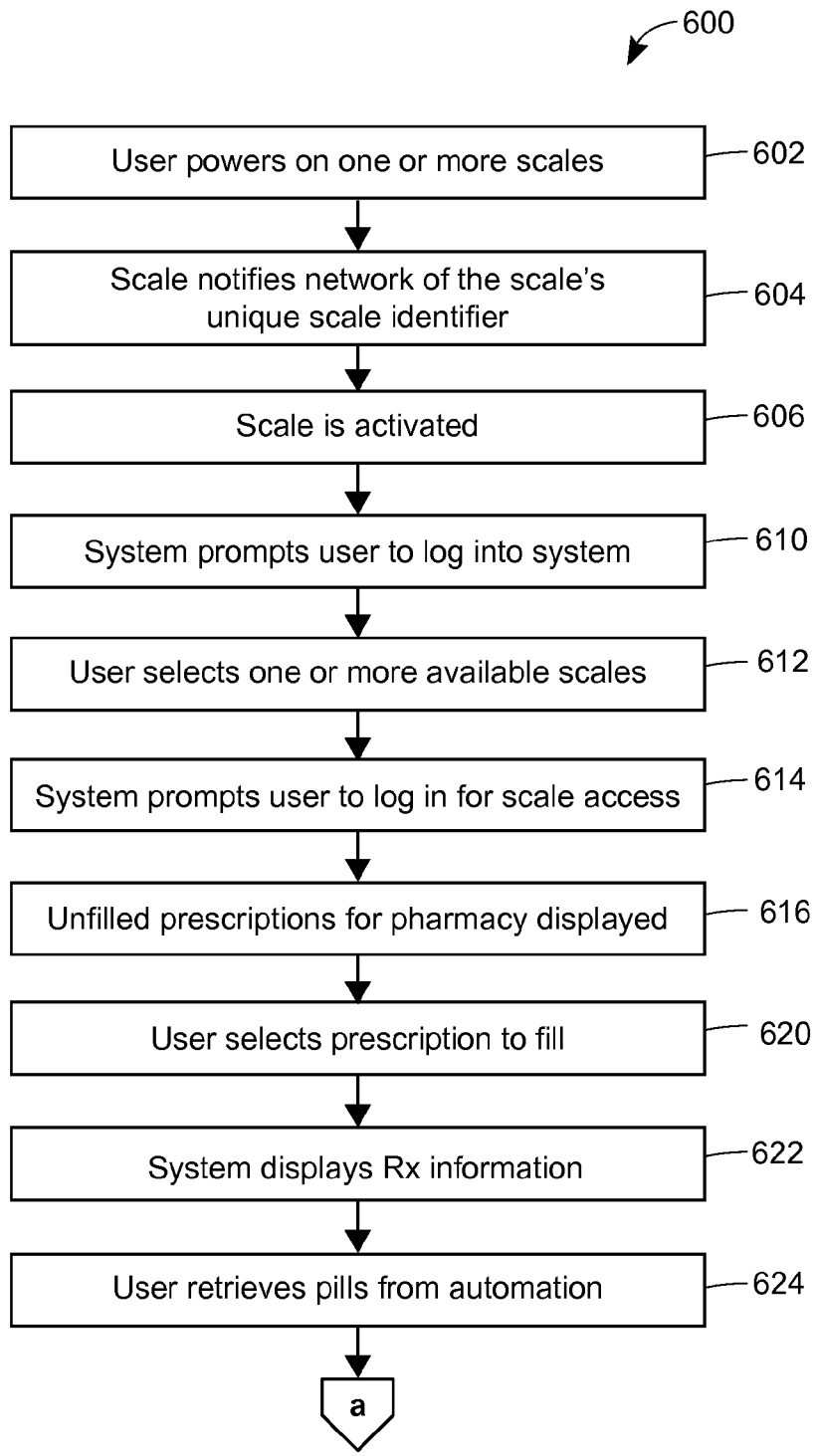
FIGS. 10A and 10B are two parts of a flowchart showing some of the steps used in another alternative embodiment to check if a correct amount of a drug has been used to fill a prescription.
Figure 10B:
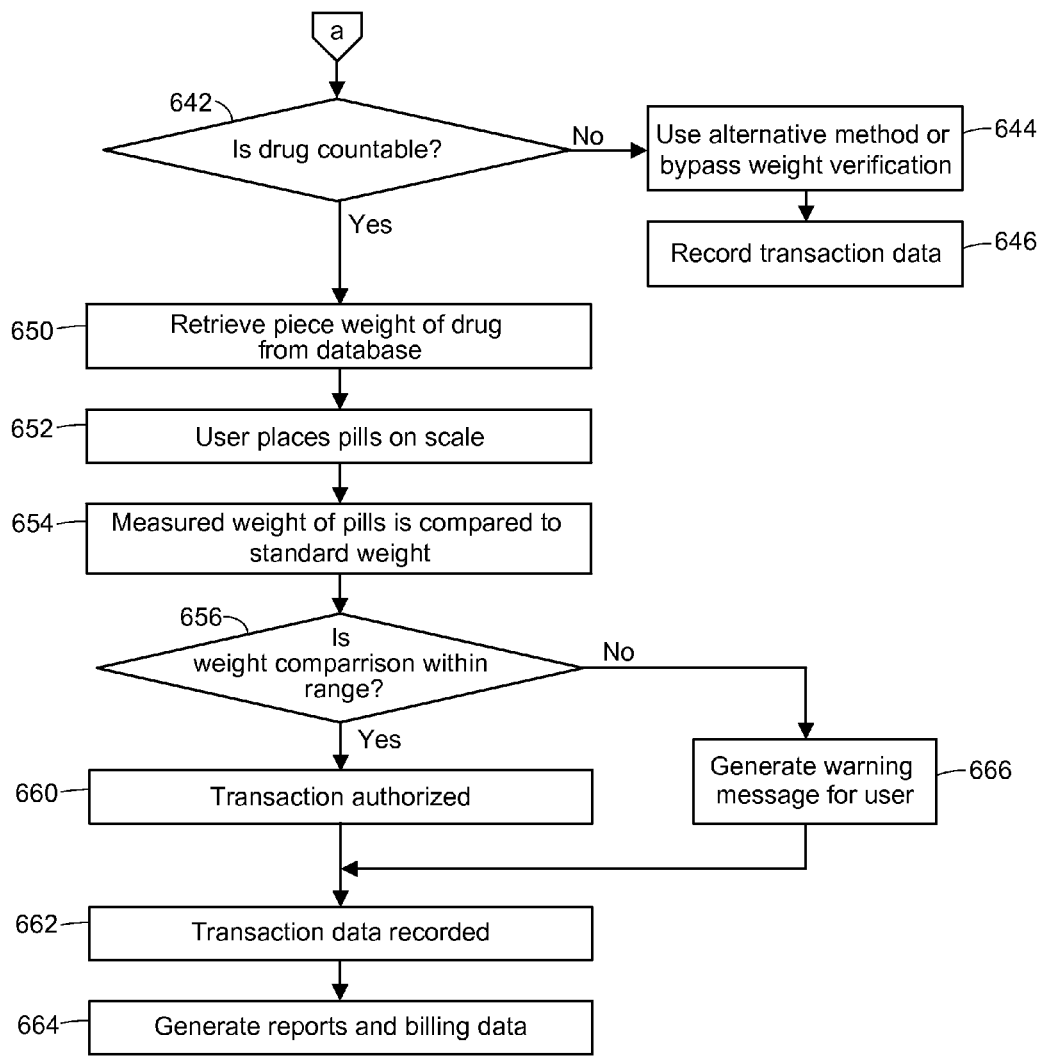

FIGS. 10A and 10B are key parts of a flowchart 600 described some of the steps used to reduce the number of errors in filling a prescription by verifying the quantity of the drug portioned by the pharmacy employee from a stock container for the drug. Some of the steps shown in the flowchart 600 may be stored in the memory of the controllers 100 and 140.

Referring to FIG. 10A, the flowchart 600 may begin when a pharmacy employee powers on one of the electronic scales 166 (block 602). The scale 166 may be adapted to notify the local server 36 via the network 152 of the scale's initialization and of the scale's unique scale identifier (block 604). Once the scale identifier for the scale 166 has been transmitted to the local server 36, the system may then activate the electronic scale 166 (block 606). The system may then update a database to indicate that the electronic scale 166 is available.

When a pharmacy employee wishes to fill a prescription, the system may prompt the pharmacy employee to log into the system (block 610) which may include a request for a user ID and password or biometric data. Once authorized login information has been submitted to the system, a desktop may appear that includes a number of buttons corresponding to available electronic scales 166. The pharmacy employee may then select one or more of the available scales by selecting the scale(s) on the employee's desktop (block 612). After selecting a scale to access, the system may prompt the pharmacy employee to login again or to provide biometric data for access to a particular electronic scale 166 (block 614). The system may then check to ensure that the scale 166 selected by the pharmacy employee is available.

Once the pharmacy employee has been granted access one or more of the electronic scales 166, the system may display on the display 154 a list of unfilled prescriptions for the local pharmacy 20 (block 616). Using a mouse, touch screen, or other input device, the pharmacy employee may select a prescription to fill from the list of unfilled prescriptions displayed on the terminal 154 (block 620).

The system may then retrieve a set of data associated with the prescription from the database and display the set of data to the user on the display 154 (block 622). The system may then check the pharmacy's inventory for an availability of the drug and the prescription. The pharmacy employee may then select a stock container associated with the drug and the prescription (block 624).

As shown in FIG. 10B the system may then determine if the drug is countable (block 642). If it is determined at the block 642 that the drug is not countable, the pharmacy employee may use an alternative method to verify the quantity of the drug portioned by the pharmacy employee from the stock container or be allowed to bypass the weight verification process (block 644). The system may then record data associated with the transaction (block 646).

If it is determined at the block 642 that the drug is countable, the system may retrieve the piece weight of the drug from a database to use in calculating a standard weight for the drug and the prescription (block 650). The pharmacy employee may then place a portioned amount of the pills on the scale 166 for measurement (block 652). The system may then compare the measured weight of the plurality of pills to the standard weight, which is a predicted total weight of the plurality of pills (block 654).

The system may then determine if the weight comparison is within an acceptable range (block 656). If it is determined at the block 656 that the weight comparison is within an acceptable range, the system may generate an authorization for the transaction (block 660). Data associated with the transaction may then be recorded (block 662) and made available during the generation of number of reports (block 664). If it is determined at the block 656 that the weight comparison is not within an acceptable range, the system may generate a warning message for the user (block 666).

Although the technique for checking the accuracy of a prescription fill, as described herein, is preferably implemented in software, it may be implemented in hardware, firmware, etc., and may be implemented by any other processor associated with the pharmacy and other facilities. Thus, the routine(s) described herein may be implemented in a standard multi-purpose CPU or on specifically designed hardware or firmware as desired. When implemented in software, the software routine(s) may be stored in any computer readable memory such as on a magnetic disk, a laser disk, or other storage medium, in a RAM or ROM of a computer or processor, etc. Likewise, the software may be delivered to a user or process control system via any known or desired delivery method including, for example, on a computer readable disk or other transportable computer storage mechanism or over a communication channel such as a telephone line, the Internet, etc. (which are viewed as being the same as or interchangeable with providing such software via transportable storage medium).

The invention has been described in terms of several preferred embodiments. It will be appreciated that the invention may otherwise be embodied without departing from the fair scope of the invention defined by the following claims.

What is claimed:

1. A method of checking the accuracy of a prescription fill comprising:
    activating an electronic scale operatively coupled to a network, the network including a plurality of operatively coupled electronic scales and a plurality of pharmacy computers;
    accessing, via one of the plurality of pharmacy computers, a prescription to fill;
    displaying to a user a set of data associated with the prescription;
    selecting an appropriate stock container corresponding to the prescription from a plurality of available stock containers, wherein the stock container contains a drug corresponding to the prescription;
    causing data to be entered that is associated with a stock container selected by the user;
    causing one of the plurality of pharmacy computers to automatically determine if the stock container selected by the user is the correct stock container to fill the prescription by automatically determining if the drug corresponding to the selected stock container is the appropriate drug for the accessed prescription;
    retrieving a piece weight of the drug from the selected stock container from a memory, the memory operatively coupled to the network;
    measuring a weight of a plurality of pills to be dispensed corresponding to the drug in the prescription;
    causing one of the plurality of pharmacy computers to compare the measured weight of the pills to be dispensed to a standard weight, the standard weight equaling a predicted total weight of the plurality of pills;
    causing one of the plurality of pharmacy computers to determine if the comparison is within an acceptable range; and
    causing one of the plurality of pharmacy computers to generate an automated authorization for the prescription fill if it is determined that the stock container selected by the user is the correct stock container to fill the prescription and if the comparison is within the acceptable range.

2. The method of claim 1, further comprising causing one of the plurality of pharmacy computers to prompt a user to provide login information to access the network.

3. The method of claim 1, further comprising causing one of the plurality of pharmacy computers to check a local inventory for an availability of the drug in the prescription.

4. The method of claim 1, wherein causing data to be entered that is associated with the stock container comprises positioning a radio frequency (RF) ID tag on the stock container in proximity of an RFID tag reader.

5. The method of claim 1, further comprising displaying to the user plurality of unfilled prescriptions to be filled at a pharmacy.

6. The method of claim 1, further comprising causing one of the plurality of pharmacy computers to generate an override report for prescriptions filled at a pharmacy that did not have authorizations generated.

7. The method of claim 1, wherein at least two of the plurality of operatively coupled electronic scales are located at geographically separate pharmacies.

8. The method of claim 1, wherein causing data to be entered that is associated with the stock container comprises scanning a barcode on the stock container corresponding to the prescription, and further comprising causing one of the plurality of pharmacy computers to determine if the barcode is located in a memory, and retrieving the set of data associated with the prescription from the memory.

9. The method of claim 1, wherein activating the electronic scale comprises transmitting a unique scale identifier to a server computer, where at least a portion of the unique scale identifier identifies a geographic location of the electronic scale.

10. The method of claim 1, further comprising permitting the user to override the computer system and fill the prescription without the system generated authorization.

11. The method of claim 10, further comprising causing one of the plurality of pharmacy computers to prompt the user to record a reason for the override.

12. The method of claim 1, further comprising causing one of the plurality of pharmacy computers to generate a report itemizing all authorizations and reasons for overrides for the user.

13. The method of claim 1, further comprising causing one of the plurality of pharmacy computers to measure performance of the user based on the electronic scale usage statistics.

14. A method of checking the accuracy of a prescription fill comprising:

activating an electronic scale operatively coupled to a network, the network including a plurality of operatively coupled electronic scales and a plurality of pharmacy computers;

accessing, via one of the plurality of pharmacy computers, a prescription to fill;

selecting an appropriate stock container corresponding to the prescription from a plurality of available stock containers, wherein the stock container contains a drug corresponding to the prescription;

causing data to be entered that is associated with a stock container selected by the user;

causing one of the plurality of pharmacy computers to automatically determine if the stock container selected by the user is the correct stock container to fill the prescription by automatically determining if the drug corresponding to the selected stock container is the appropriate drug for the accessed prescription;

retrieving a piece weight of the drug from the selected stock container from a memory;

measuring a weight of a plurality of pills to be dispensed corresponding to the drug in the prescription;

causing one of the plurality of pharmacy computers to compare the measured weight of the pills to be dispensed to a standard weight, the standard weight equaling a predicted total weight of the plurality of pills;

causing one of the plurality of pharmacy computers to determine if the comparison is within an acceptable range; and causing one of the plurality of pharmacy computers to generate an authorization for the prescription fill if it is determined that the stock container selected by the user is the correct stock container to fill the prescription and if the comparison is within the acceptable range.

15. The method of claim 14, further comprising causing one of the plurality of pharmacy computers to check a local inventory for an availability of the drug in the prescription.

16. The method of claim 14, wherein causing data to be entered that is associated with the stock container comprises positioning a radio frequency (RF) ID tag on the stock container in proximity of an RFID tag reader.

17. The method of claim 14, further comprising displaying to the user plurality of unfilled prescriptions to be filled at a pharmacy.

18. The method of claim 14, further comprising causing one of the plurality of pharmacy computers to generate an override report for prescriptions filled at a pharmacy that did not have authorizations generated.

19. The method of claim 14, wherein causing data to be entered that is associated with the stock container comprises scanning a barcode on the stock container corresponding to the prescription, and further comprising causing one of the plurality of pharmacy computers to determine if the barcode is located in a memory, and retrieving the set of data associated with the prescription from the memory.

* * * * *